United States Patent
Clemens et al.

(10) Patent No.: US 6,551,269 B2
(45) Date of Patent: Apr. 22, 2003

(54) INTRODUCER CATHETER LEAD DELIVERY DEVICE WITH COLLAPSIBLE STYLET LUMEN

(75) Inventors: William J. Clemens, Fridley, MN (US); Douglas N. Hess, Maple Grove, MN (US); Michael L. Freiborg, New Hope, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/740,083

(22) Filed: Dec. 18, 2000

(65) Prior Publication Data

US 2002/0077583 A1 Jun. 20, 2002

(51) Int. Cl.$^7$ .................................................. A61N 1/30
(52) U.S. Cl. ..................... 604/19; 604/158; 604/164.21; 604/264; 604/525
(58) Field of Search .............................. 604/19, 164.01, 604/158, 164.08, 164.09, 164.1, 164.21, 170.01, 170.02, 264, 523, 524, 525, 528

(56) References Cited

U.S. PATENT DOCUMENTS

| 3,570,485 | A | * | 3/1971 | Reilly | 128/214.4 |
|---|---|---|---|---|---|
| 4,705,501 | A | | 11/1987 | Wigness et al. | 604/43 |
| 5,246,014 | A | * | 9/1993 | Williams et al. | 607/122 |
| 5,273,052 | A | | 12/1993 | Kraus et al. | |
| 5,318,532 | A | | 6/1994 | Frassica | |
| 5,370,640 | A | | 12/1994 | Kolff | 606/2 |
| 5,396,902 | A | | 3/1995 | Brennen et al. | |
| 5,401,244 | A | * | 3/1995 | Boykin et al. | 604/53 |
| 5,464,398 | A | | 11/1995 | Haindl | 604/280 |
| 5,618,267 | A | | 4/1997 | Palestrant | 604/53 |
| 5,807,311 | A | | 9/1998 | Palestrant | |
| 5,902,331 | A | * | 5/1999 | Bonner et al. | 607/122 |
| 6,056,719 | A | * | 5/2000 | Mickley | 604/96 |
| 6,068,610 | A | | 5/2000 | Ellis et al. | |
| 6,156,029 | A | * | 12/2000 | Mueller | 606/7 |
| 6,280,433 | B1 | * | 8/2001 | McIvor et al. | 604/524 |

FOREIGN PATENT DOCUMENTS

WO WO 01/02047 1/2001 .......... A61M/25/06

* cited by examiner

Primary Examiner—Charles G. Freay
Assistant Examiner—John F Belena
(74) Attorney, Agent, or Firm—Girma Wolde-Michael

(57) ABSTRACT

An introducer catheter used to deliver an endocardial cardiac electrode has a stylet lumen which collapses upon removal of the stylet to allow for more clearance for the lead and connector to pass when the catheter is removed after lead placement. The collapsible stylet lumen permits the introducer catheter size to be reduced to 8 or 9 French and provide for passage of a 4 French lead.

4 Claims, 1 Drawing Sheet

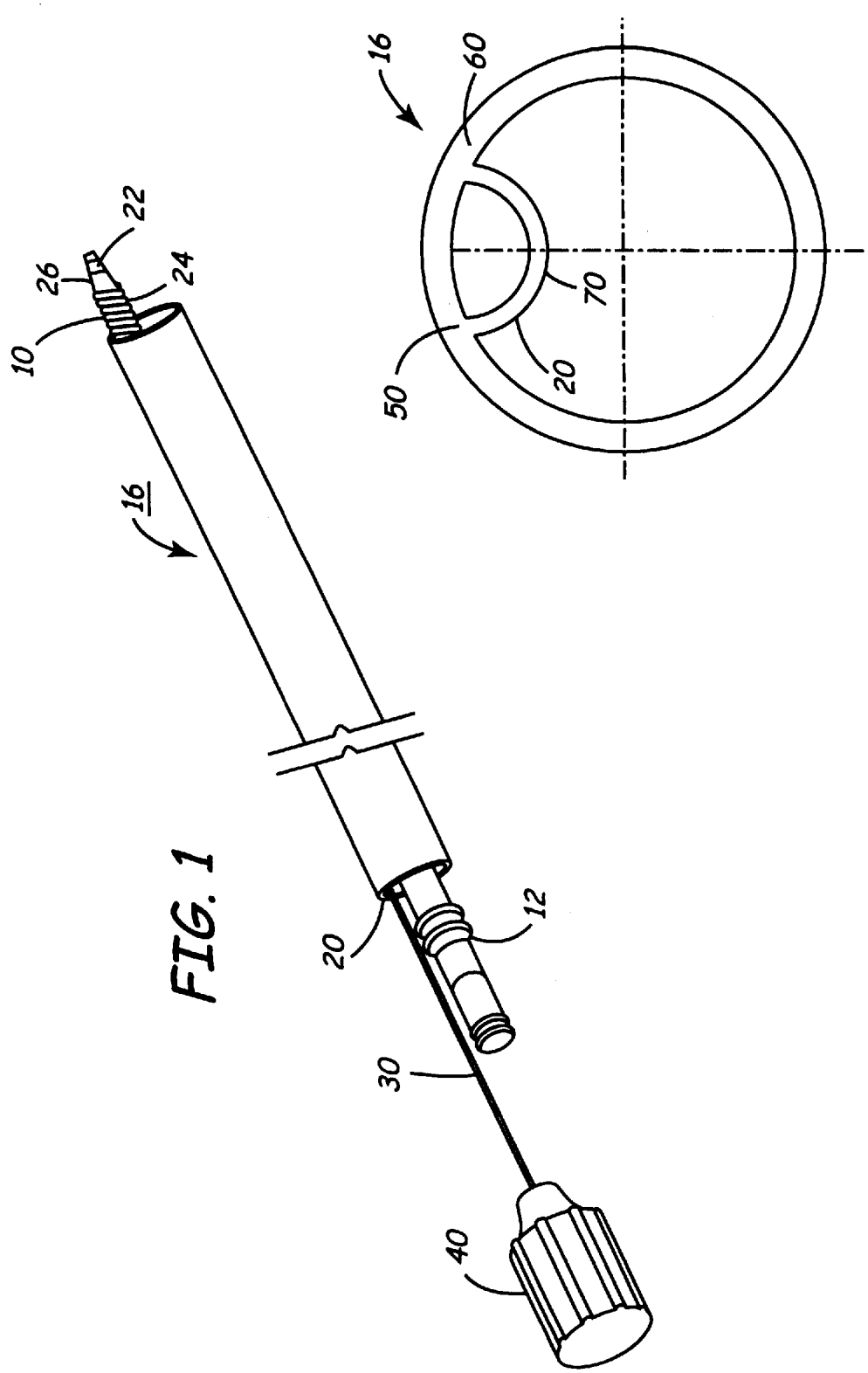

INTRODUCER CATHETER LEAD DELIVERY DEVICE WITH COLLAPSIBLE STYLET LUMEN

FIELD OF THE INVENTION

This invention relates generally to endocardial implantable cardiac leads for implantable stimulators, and more particularly to cardiac lead delivery systems using an introducer catheter.

BACKGROUND OF THE INVENTION

Implantable medical electrical stimulation and/or sensing leads are well known in the fields of cardiac stimulation, including cardiac pacing and cardioversion/defibrillation, and in other fields of electrical physiologic stimulation. In the field of cardiac stimulation, endocardial leads are placed through a transvenous route to locate one or more sensing and/or stimulation electrodes along or at the distal end of the lead in a desired location in a chamber of the heart or a blood vessel of the heart. A pacemaker or defibrillator implantable pulse generator (IPG) is typically coupled to the heart through one or more of such endocardial leads. The proximal end of such leads typically is formed with a connector which connects to a terminal of the IPG or monitor. The lead body typically comprises one or more insulated conductive wire surrounded by an insulating outer sleeve. Each conductive wire couples a proximal lead connector element with a distal stimulation and/or sensing electrode. An endocardial cardiac lead having a single stimulation and/or sensing electrode at the distal end and a single conductive wire is referred to as a unipolar lead. An endocardial cardiac lead having two or more stimulation and/or sensing electrodes at the distal end and two or more conductive wires is referred to as a bipolar lead or a multi-polar lead, respectively.

In order to implant an endocardial lead within a heart chamber, a transvenous approach is utilized wherein the lead is inserted into and passed through the subclavian, jugular, or cephalic vein and through the superior vena cava into the right atrium or ventricle. An active or passive fixation mechanism is incorporated into the distal end of the endocardial lead and deployed to maintain the distal end electrode in contact with the endocardium position. More recently, endocardial pacing and cardioversion/defibrillation leads have been developed that are adapted to be advanced into the coronary sinus and coronary veins branching therefrom in order to locate the distal electrode(s) adjacent to the left ventricle or the left atrium. The distal end of such coronary sinus leads is advanced through the superior vena cava, the right atrium, the valve of the coronary sinus, the coronary sinus, and into a coronary vein communicating with the coronary sinus, such as the great vein. Typically, coronary sinus leads do not employ any fixation mechanism and instead rely on the close confinement within these vessels to maintain each electrode at the cardiac implantation site.

Early implantable, endocardial cardiac pacing leads incorporated a lumen for receiving a stiffening stylet inside the lumen of the conductor coil. More recently, it has been proposed to diminish the lead body diameter by eliminating the lumen for receiving the stiffening stylet. Without the stiffening stylet, it is necessary to resort to use of another mechanism to pass the lead through the vessel paths identified above and to position and fix the distal end electrode of the lead at the cardiac implantation site in the heart chamber or cardiac blood vessel. One approach for implantation of small diameter endocardial leads employs an introducer catheter surrounding the lead body. The assembled introducer catheter and cardiac lead are advanced to the cardiac implantation site using a stylet carried within a stylet lumen in the introducer catheter. The introducer catheter is then retracted proximally over the lead body and proximal connector end assembly. A difficulty with use of such an introducer surrounding the cardiac lead is that permanently implantable endocardial leads are formed typically with a proximal connector end assembly having a diameter exceeding that of the lead body and conforming to an industry standard so that the connector end assembly can be fitted into and seal with an IPG connector bore conforming to the same standard. Consequently, the introducer has to be made large enough to fit over the enlarged diameter connector end assembly. Such introducer catheter size is typically about 10.5 French. This size constraint detracts from the ability to advance the introducer and lead assembly through small diameter blood vessels. Or the lead has to be made with a small diameter, non-conforming, connector end assembly or without any connector end assembly and therefore requiring connection to an adapter to be made conforming to the standard. This is inconvenient and can result in a diminished reliability.

Thus, a need remains for an introducer catheter for implanting an endocardial cardiac lead that is of a reduced diameter and yet still allows a lead and connector to easily pass therethrough.

SUMMARY OF THE INVENTION

The present invention is directed to an introducer catheter for endocardial cardiac lead delivery. In particular, the present invention provides for the reduction of introducer catheter size by implementing unique structures. Specifically, the present invention accomplishes the desired reduction by use of a bilumen catheter wherein a collapsible stylet lumen is included. The stylet lumen deforms to a collapsed condition when the stylet is removed. This allows more clearance for the lead and connector to pass through when removing the catheter.

BRIEF DESCRIPTION OF THE DRAWINGS

The advantages and features of the present invention will become better understood from the following detailed description of illustrative embodiments thereof when considered in conjunction with the drawing figures wherein:

FIG. 1 is a diagram of an introducer catheter in accordance with the present invention shown with a stylet and an endocardial cardiac lead; and FIG. 2 is a cross-section view of the introducer catheter shown in FIG. 1.

DETAILED DESCRIPTION OF ILLUSTRATIVE EMBODIMENTS

FIG. 1 shows in a generalized diagram of a lead delivery system in accordance with the present invention. An implantable endocardial cardiac lead 10 is shown extending through introducer catheter 16. Lead 10 has an elongated lead body extending from the lead connector end assembly 12 to the distal end where co-axially wound, coiled wire, lead conductors 22 and 24 are disposed. The conductors 22 and 24 are separated by an insulating sheath 26. The lead 10 is 4 French with a 0.072" connector. A lumen 20 is formed internal to the introducer catheter and receives a stiffening stylet wire 30. The stylet extends proximally from the lumen end opening so that the knob 40 may be manipulated to rotate or axially extend or withdraw the stylet wire 30 with respect to the catheter.

In FIG. 2, the introducer catheter 16 is shown in cross section to reveal the stylet lumen 20. The internal stylet lumen 20 is formed by a curved appendage attached to an inner wall of the introducer catheter at first and second points of attachment 50 and 60. Introducer catheter 16 is sized to preferably be about 8 or 9 French. It should be noted that these dimensions are given as an example and do not limit the invention to these dimensions. Practically, the introducer size may be dimensioned to include a range of various dimensions that are compatible with the lumen and stylet as implemented and disclosed herein. The stylet lumen is about 0.019" across to allow use of a standard 0.016" stylet. The lumen 20 is collapsible when the stylet wire is removed. When collapsed, neglecting the collapsed lumen wall, the interior of the catheter becomes about 0.084" across (0.065"+0.019"=0.084"). The catheter wall dimensions and the wall dimensions of the collapsible lumen are indicated in FIG. 2. It will be appreciated that the appendage that forms the stylet lumen has reduced wall thickness near the attachment points 50 and 60. The thinning of the wall thickness assists in the collapsing of the lumen. The thicker wall section 70 between the attachment points resists perforation by the stylet. If desired, a thin wall PTFE liner could be provided inside lumen 20 to further protect against perforation and reduce friction.

In use, the lead and catheter are advanced into position using the stylet to assist in placement. Once the lead is positioned and fixated, the stylet is removed from the lumen 20. When the stylet is removed, the lumen 20 collapses. With the lumen 20 collapsed, there is adequate space for the lead and connector to pass through the introducer catheter as it is pulled out.

The foregoing detailed description of a specific embodiment of the present invention has been provided for illustrative purposes. It is contemplated that various changes, alterations, and modifications may be made therein without departing from the scope and spirit of the present invention as defined by the appended claims.

What is claimed is:

1. A lead delivery apparatus, comprising:

a stylet wire;

an introducer catheter dimensioned to receive a cardiac lead therethrough and having an internal stylet lumen dimensioned to receive the stylet wire, said internal stylet lumen being collapsible upon removal of the stylet wire.

2. A lead delivery apparatus, comprising:

a stylet wire;

an introducer catheter sized and dimensioned to receive a cardiac lead therethrough, and an internal stylet lumen formed within the introducer catheter and dimensioned to receive the stylet wire, said internal stylet lumen being collapsible upon removal of the stylet wire to open the interior of the introducer catheter to permit passage of a cardiac lead and connector therethrough.

3. A lead delivery apparatus, comprising:

a stylet wire;

an introducer catheter sized and dimensioned to receive a cardiac lead therethrough, and an internal stylet lumen formed within the introducer catheter and dimensioned to receive the stylet wire, said internal stylet lumen being collapsible upon removal of the stylet wire to open the interior of the introducer catheter to permit passage of a cardiac lead and connector therethrough;

said internal stylet lumen being formed by a curved appendage attached to an inner wall of the introducer catheter at first and second points of attachment.

4. A lead delivery apparatus, comprising:

a stylet wire;

an introducer catheter dimensioned to receive a cardiac lead therethrough and having an internal stylet lumen dimensioned to receive the stylet wire, said internal stylet lumen being collapsible upon removal of the stylet wire, and said internal stylet lumen being formed by a curved appendage having a reduced wall thickness near the attachment points.

* * * * *